(12) United States Patent
Strawder (10) Patent No.: US 7,764,179 B1
(45) Date of Patent: Jul. 27, 2010

(54) METHOD OF AN APPARATUS FOR MONITORING THE PROCESSING CYCLE OF A JOB AND INSTRUCTING WORKERS TO PERFORM EVENTS OR STEPS ACCORDING TO A STANDARD

(76) Inventor: Glenn G. Strawder, 14111 Armilla Ct., Burtonsville, MD (US) 20866

( * ) Notice: Subject to any disclaimer, the term of this patent is extended or adjusted under 35 U.S.C. 154(b) by 1003 days.

(21) Appl. No.: 11/472,292

(22) Filed: Jun. 22, 2006

Related U.S. Application Data (60) Provisional application No. 60/758,920, filed on Jan. 13, 2006.

(51) Int. Cl.
*G08B 23/00* (2006.01)
(52) U.S. Cl. .............. 340/573.1; 340/3.1; 340/506; 340/527; 340/825.36; 340/825.49
(58) Field of Classification Search ............. 340/573.1, 340/506, 507, 524, 525, 527, 529, 3.1, 825.36, 340/825.49
See application file for complete search history.

(56) References Cited

U.S. PATENT DOCUMENTS

| | | | |
|---|---|---|---|
| 3,911,446 A | 10/1975 | Albertini | |
| 4,281,330 A | 7/1981 | Warrick | |
| 5,307,262 A * | 4/1994 | Ertel | 705/2 |
| 6,282,513 B1 | 8/2001 | Strawder | |
| 6,408,330 B1 * | 6/2002 | DeLaHuerga | 709/217 |
| 6,424,995 B1 | 7/2002 | Shuman | |
| 6,440,067 B1 | 8/2002 | DeLuca et al. | |
| 7,024,626 B2 | 4/2006 | Ko | |
| 2002/0133503 A1 * | 9/2002 | Amar et al. | 707/104.1 |
| 2004/0249676 A1 * | 12/2004 | Marshall et al. | 705/2 |
| 2006/0173713 A1 * | 8/2006 | Petro et al. | 705/2 |
| 2006/0247709 A1 * | 11/2006 | Gottesman et al. | 607/30 |

* cited by examiner

*Primary Examiner*—Daryl Pope
(74) *Attorney, Agent, or Firm*—William D. Hall (57) ABSTRACT

A method for recording information about a particular patient being processed through a hospital or medical facility that has a number of departments, each of which may perform a different type of procedure on a patient is described. A physician may enter an order into a computer which describes the procedure to be performed on the patient. A computer has various inputs respectively operable by different workers in various departments of the hospital to provide information about the patient and which is compared with a standard protocol for medical procedures performed in the various departments. The computer may then print out a description of the patients stay in the hospital including an variations from the standard protocol.

12 Claims, 7 Drawing Sheets

Fig. 1

Remember To Complete

Exam # CT-06-00123

When Finish!

Fig. 2

Attention!

Pass Code [John Doe]

You Started But Have Not Completed or Reset

Exam # CT-06-00123

Please Change is Current Status! 327
[OK]

Fig. 3

Stop!

Someone Immediately Complete or Reset

Exam # CT-06-00123

Enter Your Pass Code to Receive Credit: [Jane Doe] —34    [Accept]

Fig. 4

EXAM NOT COMPLETED
STANDARD & SEVERE WARNING
REPORT

Modality: CT Scan          Shift: 1

| Start | | End | |
|---|---|---|---|
| Date | Time | Date | Time |
| January 17, 2006 | 0700 | January 17, 2006 | 1400 |

Standard Warnings = 1

| Number | Exam Name | Exam Ordered Date -- Time | Tech Started Exam | Exam Started Date -- Time | Standard Warning Time |
|---|---|---|---|---|---|
| 1 | CT Head Scan | 1/17/06  0702 | Dave Jones | 1/17/06  0710 | 0731 |

22⌐         ⌐14         ⌐16  ⌐18

Severe Warnings = 1

| Number | Exam Name | Tech Started Exam -- Time | Severe Warning Time | Tech Accepted Warning -- Time | Exam Completed Time |
|---|---|---|---|---|---|
| 1 | CT Head Scan | Dave Jones  0710 | 0741 | Jane Doe  0742 | 0744 |

EXAMINATION PROCESSING CYCLE STATUS REPORT

Examination Name: CT Head Scan
Examination Accession #: CT-06-00123 ⟵14

12⟶ Date: Jan. 17, 2006          Time: 0702

| 11⟶ Ordered | 13⟶ Started | 15⟶ Completed | 17⟶ Dictated | 19⟶ Transcribed | 21⟶ Finalized | 23⟶ Reimbursed |
|---|---|---|---|---|---|---|
| [X] | [ ] | [ ] | [ ] | [ ] | [ ] | [ ] |

16⟶ Date: Jan. 17, 2006          18⟶ Time: 0702

| Ordered | 13⟶ Started | Completed | Dictated | Transcribed | Finalized | Reimbursed |
|---|---|---|---|---|---|---|
| [ ] | [X] | [ ] | [ ] | [ ] | [ ] | [ ] |

Date: Jan. 17, 2006          Time: 0710

| Ordered | Started | 15⟶ Completed | Dictated | Transcribed | Finalized | Reimbursed |
|---|---|---|---|---|---|---|
| [ ] | [ ] | [X] | [ ] | [ ] | [ ] | [ ] |

HISTORY REPORT

Modality: [X-ray/CT Scan]  Shift: [1]

| | Start | | End | |
|---|---|---|---|---|
| | Date | Time | Date | Time |
| | [Jan. 1, 2006] | [0000] | [Jan. 1, 2006] | [2359] |

| Modality | # Reminders | # Warnings<br>15, 3, 19, 21,<br>Completed-Dictated-Transcribed-Final | # Commanding Warnings<br>15, 3, 19, 21,<br>Completed-Dictated-Transcribed-Final |
|---|---|---|---|
| X-ray | [182] | [25] [18] [14] [23] [11] [4] | [15] [3] [19] [21] [13] [8] [4] [7] |
| CT | [152] | [20] [12] [4] | [9] [5] [10] [15] |

Fig. 7

METHOD OF AN APPARATUS FOR MONITORING THE PROCESSING CYCLE OF A JOB AND INSTRUCTING WORKERS TO PERFORM EVENTS OR STEPS ACCORDING TO A STANDARD

I claim the benefits of my prior Provisional Application Ser. No. 60/758,920 filed Jan. 13, 2006 entitled A Method For Monitoring And Instructing The Medical Team Involved In Performing Parts Of A Medical Examination's Cycle.

BACKGROUND OF THE INVENTION

In a modern hospital, the personnel of each medical department such as Laboratory, Radiology, etc. all employ electronic information systems to help them order and track the progress or status change of the type of procedures that they perform on a patient. Each department have many different types of procedures they perform. Each procedure has its own number of routine events or steps that must be performed to complete its processing cycle. Both clerical and technical workers are involved in performing the various events or steps in the processing cycle. The procedure will next be described by describing how a CT scan has been performed.

Typically a physician will call a department to order a particular test to be performed on a certain patient. The receptionist of the department will then enter the procedure ordered on the patient into their department information system. This is the first event or step in the processing cycle of any procedure or test. The ordered procedure may show up in the form of a computer paper out print or on a computer display screen. Next, a technologist sees the patient's procedure is in the "order status" goes and gets the patient from a waiting area then brings the patient into an examining room to perform the procedure. Before starting to perform the procedure the technologist enters data into the department's information system which changes the procedure's status from "ordered" to "started" and indicates to other technologists that the procedure is being performed. Once the technologist has finished performing the procedure, he immediately enters data into the department's information system which now changes the procedure's processing cycle's status again. This time the data that is entered into the department's information system changes the procedure's status from "started" to "completed" and shows that the technologist has finished performing the procedure and the next event, or step in the cycle, can be performed. Next, a radiologist sees on a display computer screen of the department's information system that this particular procedure is in the "completed status" which indicates to him that it is ready to be dictated or interpreted by a radiologist. Before the radiologist begins to read the procedure he now enters data into the department's information system which changes the procedure's status from "completed" to "started dictation".

In my prior patent (U.S. Pat. No. 6,282,513) I teach that a standard protocol examination (such as a CT scan) can be recorded in a computer and the actual results of the examination is compared to the standard and a result is printed out.

SUMMARY OF THE INVENTION

The acronym "HIS" stands for Hospital Information System.

The acronym "DIS" stands for Department Information System.

The word "HL-7" refers to the seventh level of standardizing electronic digital data in the medical computer community. The word "HL-7 message" refers to a standardize digital piece of data, etc.

The word "procedure" refers to any type of medical test, examination, treatment process or job related to or performed on a patient.

The word "CT procedure"" refers to an examination or treatment that uses a Computerized Axial Tomography machine.

The word "treatment" refers to the application of medical care to a patient.

The word "unit" refers to any medical treatment facility, and without limiting the aforesaid definition of "unit", includes a facility such as a laboratory, an emergency room as well as any sub-department such as X-ray, MRI, CT Scan, etc in a medical facility.

The word "treatment" refers to both the procedure ordered on a patient and the processing cycle associated with the procedure.

The word "unit" refers to any medical treatment facility, and without limiting the aforesaid definition of "unit" includes a facility such as a laboratory, an emergency room as well as any sub-department such as X-ray, MRI, CT Scan, etc in a medical facility.

The word "processing cycle" refers to the series of clerical and technical events or steps involved starting with creating the order to perform the procedure to preparing the bill for the procedure that must be performed.

The word "professional group" refers to members of the same group such as all receptionists, all nurses, all technologists, all physicians, all transcribers, etc.

The word "ordered" refers to the event or step of entering data into a DIS that produces the paperwork for a requested procedure to be performed on a patient.

The word "started" refers to the event or step of entering data into a DIS to indicate that the technical performance of a particular procedure has begun.

The word "completed" refers to the event or step of entering data into a DIS to indicate that the technical performance of a particular procedure is finished.

The word "event" refers to the step or part of a processing cycle that is performed by a worker such as, the receptionist entering data into an information system to create the order for a procedure to be performed on a patient.

This invention sets forth new procedures for running a hospital or other medical facility that has one or more departments. A few examples of such departments include radiology, cardiology, laboratory, physical therapy, emergency room, etc.

Each department has standard procedures that are practiced many times daily, for example the radiology department has standard x-ray procedures for each main part of a human body and also has CT scans for each main parts of the body. Another example is that the cardiology department has many procedures, examples of which comprise an EKG, a sonic study of the heart and a sonic study of the amount of plaque in the arteries of a patient.

Each of the procedures in each of the many departments may be provided according to this invention, with a standard protocol for the various events or steps involved in the processing cycle of the procedure. The actual performance of a procedure by the skilled technologist who performs such procedure may also be included.

The invention also contemplates a computer (having a memory) which stores not only all of the procedures in each and every department and may also receive entries from not only the physicians who order the procedures but also the work done by each worker including each technologist as he or she performed his or her parts of the overall procedure.

Let us now assume that a patient enters the hospital. The patient's physician then issues an order to the computer identifying the various procedures to be performed on the patient. If there is some importance in having one specific procedure precede another or be performed no later than a time the physician will so specify. The physician may also specify that an additional procedure is to be performed if the outcome of another procedure yields a certain result.

The computer causes the desired procedures to be performed in accordance with the physician's order. If any of the various workers of a department involved in performing some part of the procedure's processing cycle do not perform a particular event or step in the process correctly or within a time limit, the worker who has failed to comply will first receive a warning and later (if still not in compliance) a command that he comply.

The computer may unless otherwise instructed, schedule a patient's various procedures in the particular order that best fist into the backlog of patients for the various procedures in the physician's order, unless the physician specifies a particular order for the procedures.

A technologist when entering into the computer what he has done for a patient, may also enter relevant billing information to thereby expedite preparation of the statement of accounts.

The computer will compare the standard protocol with the entries of any of the various professional groups in a department such as technologist, receptionist, etc. and determine any differences. These differences will be stored in said memory. For examples, each procedure will have a standard time (for example 10 minutes) for the performance of the procedure. This standard time will be compared with the time the technologist entered as the time he took to perform the procedure.

If a technologist takes longer than the standard time for performing a procedure, the technologist may also enter the reason for the extra time. If this reason is something for which the hospital normally charges an extra fee the technologist will enter sufficient details into the computer to assure the added work is reflected in the bill.

Moreover, it is possible in many hospitals for a patient to be "forgotten" either from a worker that moved the patient to a certain location and forgot they were still there or a worker misplaces an outpatients order under other documents and forgets that the patient is still waiting. The present computer is however kept informed of just where a patient is located at any given time and if a patient remains at a given location for more than a specified time the computer will inform appropriate officials of the matter so that action may be taken accordingly.

DETAILED DESCRIPTION OF THE INVENTION

The following description is divided into three parts, namely: (1) How to set up the system in a typical hospital, (2) How to use the system with an explanation as to how to apply the system to a given patient, and (3) Typical printout of how the system worked on the given patient.

In the prior art, there are many different departments in a hospital such as Laboratory, CT Scan, MRI Scan, X-ray, Cardiology, etc. Each department employs "an electronic information system" to help them order procedures and track the progress or status change of a procedure during its processing cycle. Each department has many different types of procedures it performs. Each procedure has a number of standard events and steps in its processing cycle. Each department employs both clerical and technical workers that perform the standard events and steps of the processing cycle of a procedure, and enter into their information system the correct response, and in a timely manner. A patient may need to have one or more procedures performed by one, some or all departments in a hospital.

(1) Setting Up the System

When the invention is first installed, either it has the standard protocols in it created by the provider of the system or the hospital's manager will create one or more standard protocols.

Figure 1:
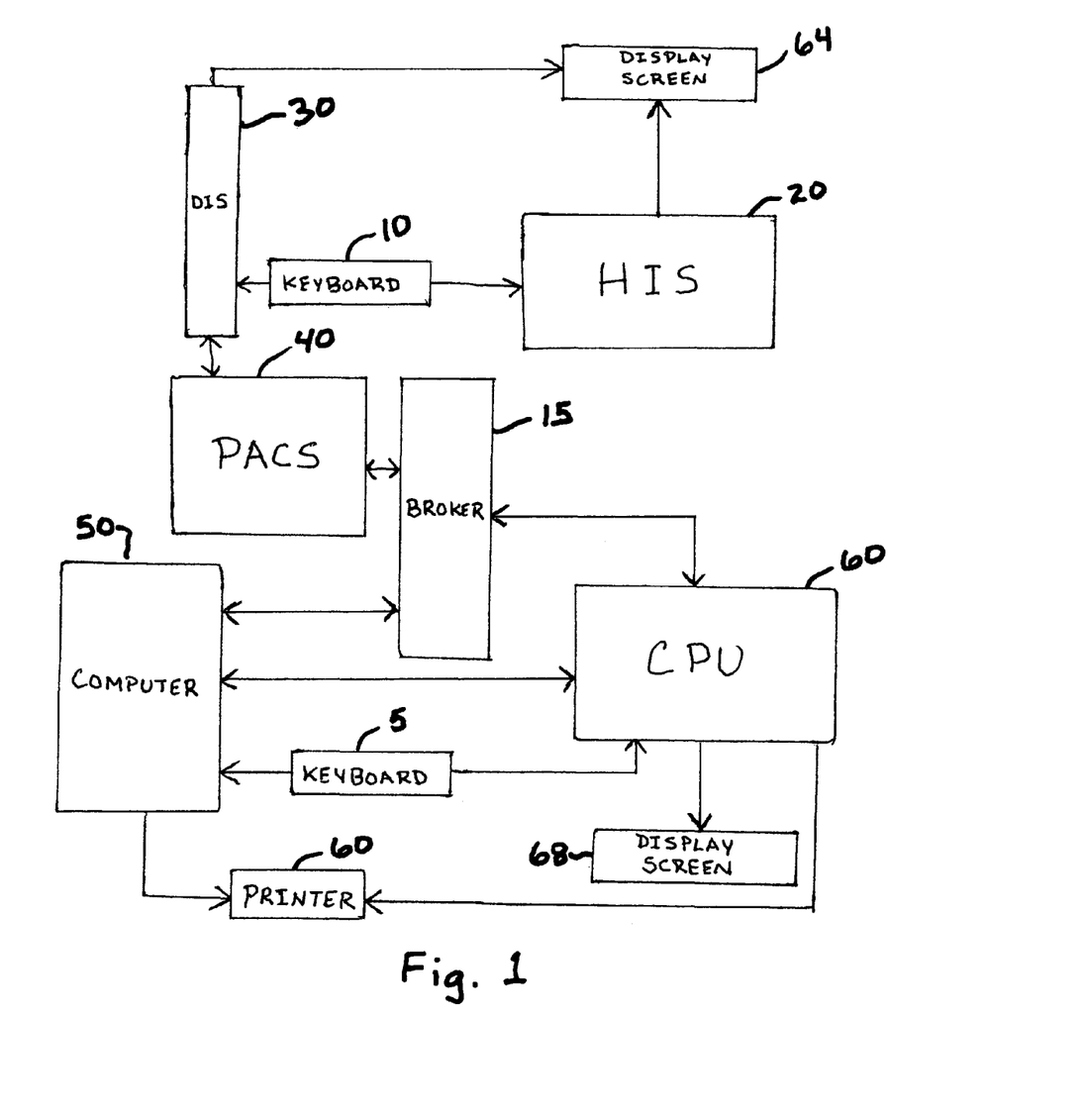
FIG. 1 is a block diagram of the apparatus for practicing the invention.

The following is a description of the steps a CT manager may take to enter data into the invention's computer 50 or CPU 60 to create a standard protocol.

This is done originally when the system is first installed, and may be updated from time to time.

First, a CT manager turns on computer 50 and CPU 60 by pressing a button labeled "on" (not illustrated). Next, the CT manager may log into the system in the standard manner by entering a personal password codes via keyboard 5 and then pressing the "accept" button.

Data may be entered by touching a soft key (not illustrated) located on display screen 68 of the invention. Data may also be entered via any other known method or means such as voice recognition, etc.

Next, the CT manager may view on display screen 68 a menu which lists various available options. One option would be to call up a standard protocol programmed by the manufacturer. Another option could be for the CT manager to create his own personal standard protocol. In this example, the CT manager wants to create a standard protocol for the amount of time it should take a CT technologist to complete a particular type of procedure on a patient once they have started to perform the procedure.

The CT manager via keyboard 5 selects from a list the "create a standard protocol" option and then presses the "accept" button. Next, the CT manager selects from a list the particular procedure the standard is being created for and then presses the "accept" button. In this example, the "procedure 22" is a CT head scan.

Now, the CT manager via keyboard 5 may select, from a list, the particular event or step during the processing cycle of "procedure 22" that they want to create a standard protocol for. In this example, the event is the amount of time that it should take a worker (technologist) to complete the "procedure 22", once the worker has entered data into HIS 20, DIS 30 or computer 50 (CPU 60) that indicates they are now starting to perform "procedure 22". In this example, the amount of time is 10 minutes. The CT manager for example via keyboard 5 enters into computer 50 (CPU 60) 10 minutes as the standard amount of time to complete "procedure 22".

Next, the CT manager via keyboard 5 enters into computer 50 or CPU 60 the standard amount of time computer 50 or CPU 60 should wait before it sends a reminder message to a worker once the worker has entered data into DIS 30 that indicates they have started to perform "procedure 22". Computer 50 or CPU 60 may be programmed to send a screen shot reminder message (see FIG. 2) that appears on display screen 64 to help a worker remember to perform their next duty, coming up in the processing cycle, correctly.

Figure 3:
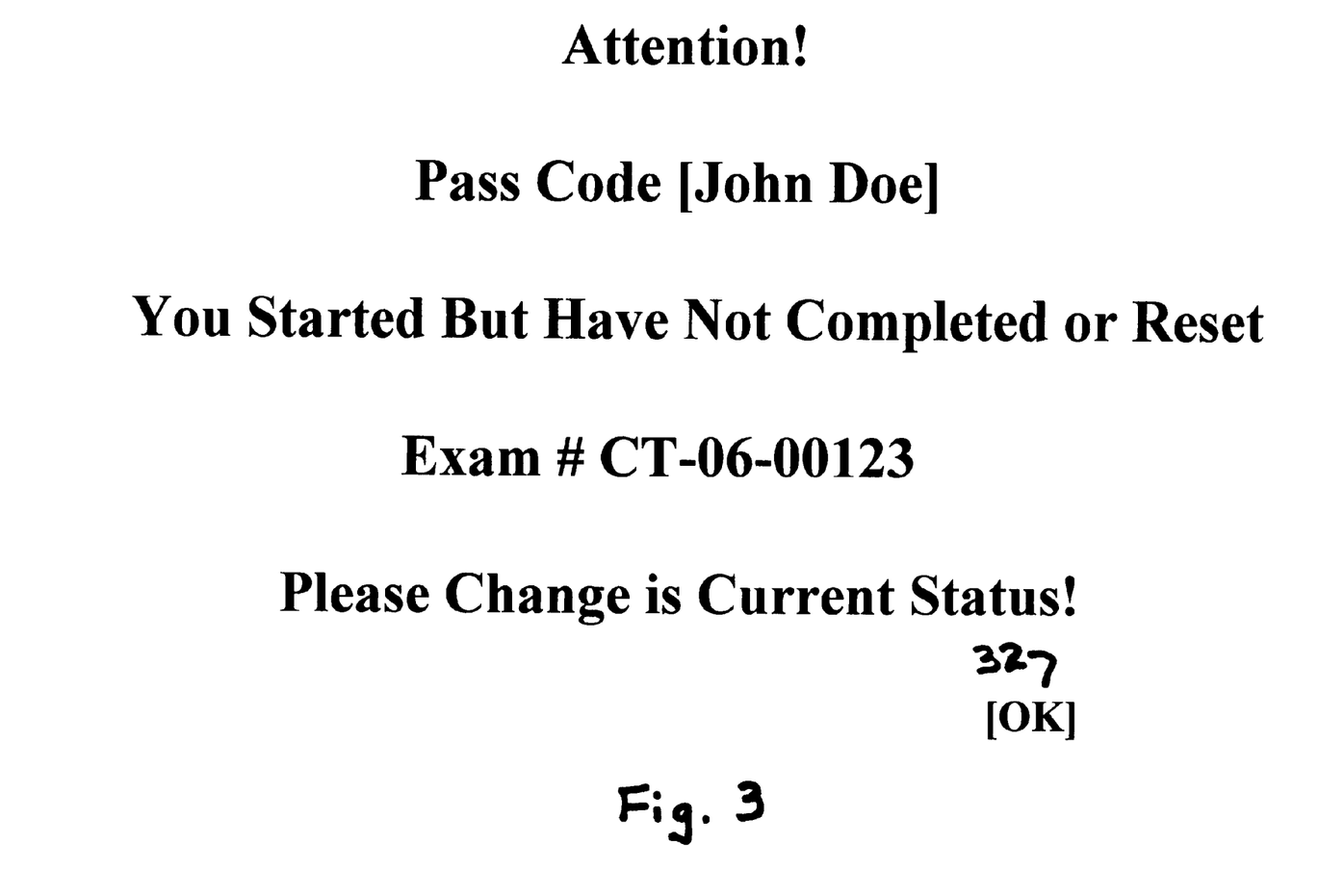
FIG. 3 is a computer screen shot of a warning message made with the apparatus of FIG. 1.

Next, the CT manager via keyboard 5 enters into computer 50 or CPU 60 the standard amount of time computer 50 or CPU 60 should wait before it sends a warning message to a worker that the "procedure 22" was started 13 but has not yet been completed 15. Computer 50 or CPU 60 may be programmed to send a warning message (see FIG. 3) that appears on display screen 64 that indicates that the standard protocol after the procedure 22 was started has not be performed.

In this example, the standard amount of time entered by the manager for computer 50 to wait until it sends a warning message (see FIG. 3) to either change the status of "procedure 22" from start 13 to "completed" 15 or reset the status of "procedure 22" back to the status of "order" 11, is going to be 20 minutes from the time "procedure 22" status is changed to the "started" 13 and has not been changed to the status of "completed" 15.

Next, the CT manager via keyboard 5 enters into computer 50 or CPU 60 data that represents the standard amount of time computer 50 or CPU 60 should wait before it sends a commanding message to a worker or a member of the worker's professional group that a warning message has already sent to the worker about the status of "procedure 22" and still no appropriate response has not been made, and to either change its current status of "started" 13 to the status of "completed" 15 or reset the procedure's status back to the "ordered" 11 status.

In this example, the CT manager entered 20 minutes as the standard amount of time that computer 50 waits before it sends a commanding message (see FIG. 3) after it has already sent a worker or professional group a warning message about an event that still has not been performed according to standard.

In the summary of the description of the heading, it is noted that the standard procedure may be entered into computer 50 for every event or step performed in processing a patient, in departments of a hospital or medical facility, so that when actual patients are treated, their treatment may be compared to the standard protocol.

Similar test and procedures would be applied whether the patient was an outpatient who came to the hospital or an inpatient who is in a bed, in a room at the hospital.

(2) One Way the System May be Used

After the standard protocol is entered by the CT manager, assume a patient entered a hospital equipped with the invention and was treated accordingly. A physician ordered several tests to be performed on the patient in multiple departments such as: (a) a CT head scan, (b) a MRI chest scan, (c) a Lab blood tests, (d) a TB test to be performed by the Lab, and (e) an EKG by the Cardiology department. There is an order in which these different procedures should be performed and the patient is scheduled to have them accordingly. The order in which the tests are scheduled is determined not only in accordance of the backlog of work in each department but also as required by the medical requirements of the patient. A nurse or other person then enters into the computer the procedures and the order in which the procedures are to be performed. Each of said procedure and/or procedures is one which has the standard method of performing the same including the expected time interval that is required to perform a typical such procedure and the time interval that is required to complete the entire processing cycle of a procedure.

If the patient is scheduled to have the Lab test first, and if the computer's memory shows a backlog of patients are already waiting for Lab tests, the patient is then rerouted to go get the CT scan first and then maybe directed to have the MRI next, if the Lab still has a backlog of patients at the time.

Each department will report to the computer their patient schedule and backlog times and keep the computer informed with this information so the computer can adjust accordingly.

Unless the physician says that one of the procedure's ordered on the patient should precede another, and unless he gives instructions to the contrary, the computer will figure out the order and schedule the events in an order consistent with the backlogs of the various persons or departments involved.

A receptionist in the CT department greets a new patient on arrival and enters the necessary data into HIS 20 or DIS 30 via keyboard 10 or computer 50 via keyboard 5 that creates the order for the CT head scan or "procedure 22" and presses the "accept" button. CT head scan or "procedure 22" is now a file document and is in the status position of "ordered" 11 (see FIG. 6) of the processing cycle. The data that the receptionist entered to create the examination's order into HIS 20 and DIS 30 is then downloaded to computer 50 via broker 15. Computer 50 or CPU 60 may be integrated with HIS 20 or RIS 30 so the need to download the data inputs or status changes for "procedure 22" is eliminated. Computer 50 compares the data entered to a standard protocol in its memory.

If the result of the comparison shows that the receptionist performed her event correctly, computer 50 may send to display screen 64 a reminder message for her to remember to do a future event, if a future event is needed. However, if the result of the comparison shows that the receptionist did not perform her event according to, a standard, computer 50 may send to the reception's display screen 64 a warning message instructing her to correct this wrong doing. It should be understood that there are many inputs or actions of the receptionist that may cause computer 50 to send her a message that indicates she has performed an event or step incorrectly or opposite the standard. However for the sake of brevity I will only describe the one that follows. An example of this is if the receptionist entered information to create the order for "procedure 22" but did not enter the correct order number for this patient's "procedure 22", instead she gave the patient an old or used order number that was given to and already processed with a previous patient's procedure. Computer 50 will send the receptionist a warning message via display screen 64 that indicates to her that the order number she has assigned to "procedure 22" is wrong and can not be used. If the receptionist continues to try to use the wrong order number, computer 50 may send via display screen 64 a message that requires the receptionist to enter her personal pass codes to remove the message from the screen. The receptionist's pass codes will prove to management that she is the one who continued to attempt to issue a used or wrong order number despite the warning message(s) sent by computer 50. Computer 50 is capable of producing a list of the warning messages it sends and the messages that require data to be entered to remove it from display screen 64.

In a modified form, data may be entered by workers using a key punch pad that has one or more keys. Each key is may be labeled with a specific reply or response such as, one key may be labeled "start" 13 and is pressed a worker when "procedure 22" is "started" 13, while another key may be labeled "completed" 15 and is pressed by a worker when "procedure 22" is finish.

Once the receptionist has performed her event(s) correctly and placed CT head scan or "procedure 22" in the "ordered" 11 status (see FIG. 6), this will indicate to the next worker in line (which is the technologist) it is ok to perform their events or step in the processing cycle.

If the patient is required to wait more then the standard amount of time once a procedure is in the "ordered" 11 status position in computer 50, computer 50 may send in this case a message to both the receptionist and the technologist that will perform "procedure 22" showing that the patient has been waiting longer then the standard time period to have the procedure performed.

If the wait continues beyond some specific time period, computer 50 may send the receptionist and the technologist a more emphatic message that the patient has been waiting longer then desired.

If the patient waits longer than the standard amount of time once "procedure 22" is in the "ordered" 11 status position in computer 50, computer 50 may send a message to both the receptionist and the technologist that will perform "procedure 22" to extend the patient's scheduled procedure time further.

A technologist sees on display screen 64 that "procedure 22" is now in the "ordered" 11 status position in computer 50 and immediately locates the patient and brings them into an examining room to perform "procedure 22".

The technologist next enters data into DIS 30 via keyboard 10 to change the current status of "procedure 22" from the "ordered" 11 status position to the "started" 13 status position. The data that the technologist entered to change the current status of "procedure 22" from the "ordered" 11 status position to the "started" 13 status position is download to computer 50 or CPU 60 via broker 15. Computer 50 compares the downloaded data about the status change to a standard protocol in its memory. If the result of the comparison shows that the technologist performed his event correctly, computer 50 may send to display screen 64 a reminder message for him to remember to stay alert and not to forget to perform a future event (see FIG. 2). However, if the result of the comparison shows that the technologist took longer then the standard time to perform "procedure 22" or entered the wrong data (did not perform his event according to the standard), computer 50 may send to display screen 64 a warning message instructing him to correct this matter.

The technologist may also enter that he made three series of scans, one series was the scout scan for setting up the slices, one series was for taking pictures of the cerebellum area of the brain, and one series was for taking pictures of the brain above the cerebellum.

Sometime later, the technologist enters data again into DIS 30, but this time the data that is entered changes the status of procedure 22 from the "started" 13 status position to the "completed" 15 status position, to show or indicate to the next worker in line he has finished performing his part of the processing cycle of procedure 22 (see FIG. 6).

Figure 2:
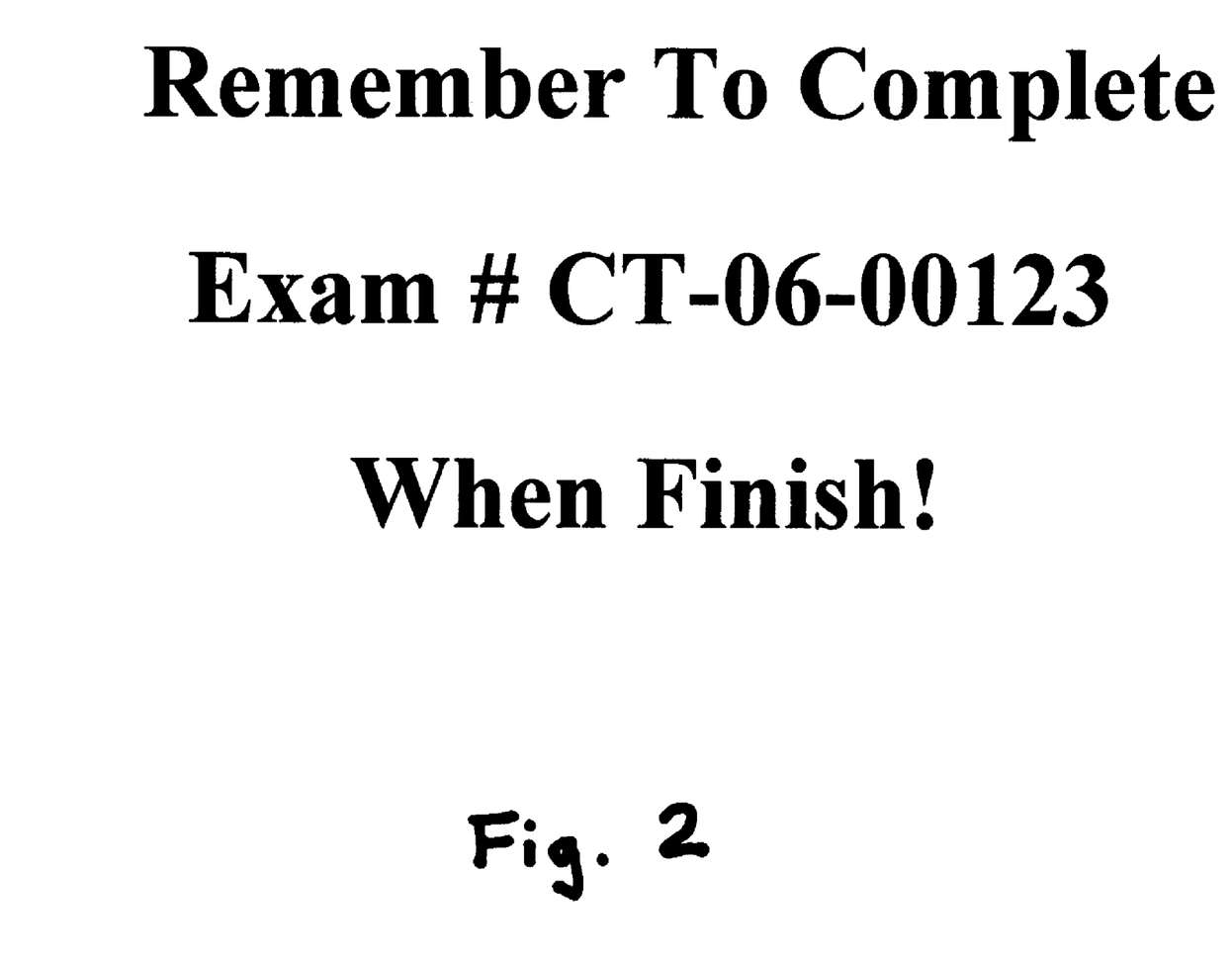
FIG. 2 is a computer screen shot of a reminder message made with the apparatus of FIG. 1.

If the result of the comparison shows that the technologist performed his event correctly, computer 50 may send to display screen 64 a reminder message for him to review the steps of the last event he performed similar to FIG. 2. However, if the result of the comparison shows that the technologist did not perform his event according to the standard, computer 50 may send to display screen 64 a warning message (see FIG. 3) instructing him to correct this matter. It should be understood that there are many inputs or actions of the technologist that may cause computer 50 to send the technologist a message that indicates he has performed an event or step opposite the standard. However for the sake of brevity I will only describe the one that follows. An example of this is if the technologist forgets to enter information into DIS 30 that will indicate to others he has finished performing "procedure 22" and the standard amount of time has passed that it would normally take to perform "procedure 22", computer 50 may send the technologist a warning message (FIG. 3) that indicates for him to change "procedure 22" status appropriately.

If the technologist does not perform the event in the warning message within a certain period of time, computer 50 may send him or his professional group of workers a commanding message (see FIG. 4) to remedy this matter. The commanding message would require the particular technologist that decides to perform the event to enter via keyboard 10 into DIS 30 there personal password codes 34.

Figure 6:
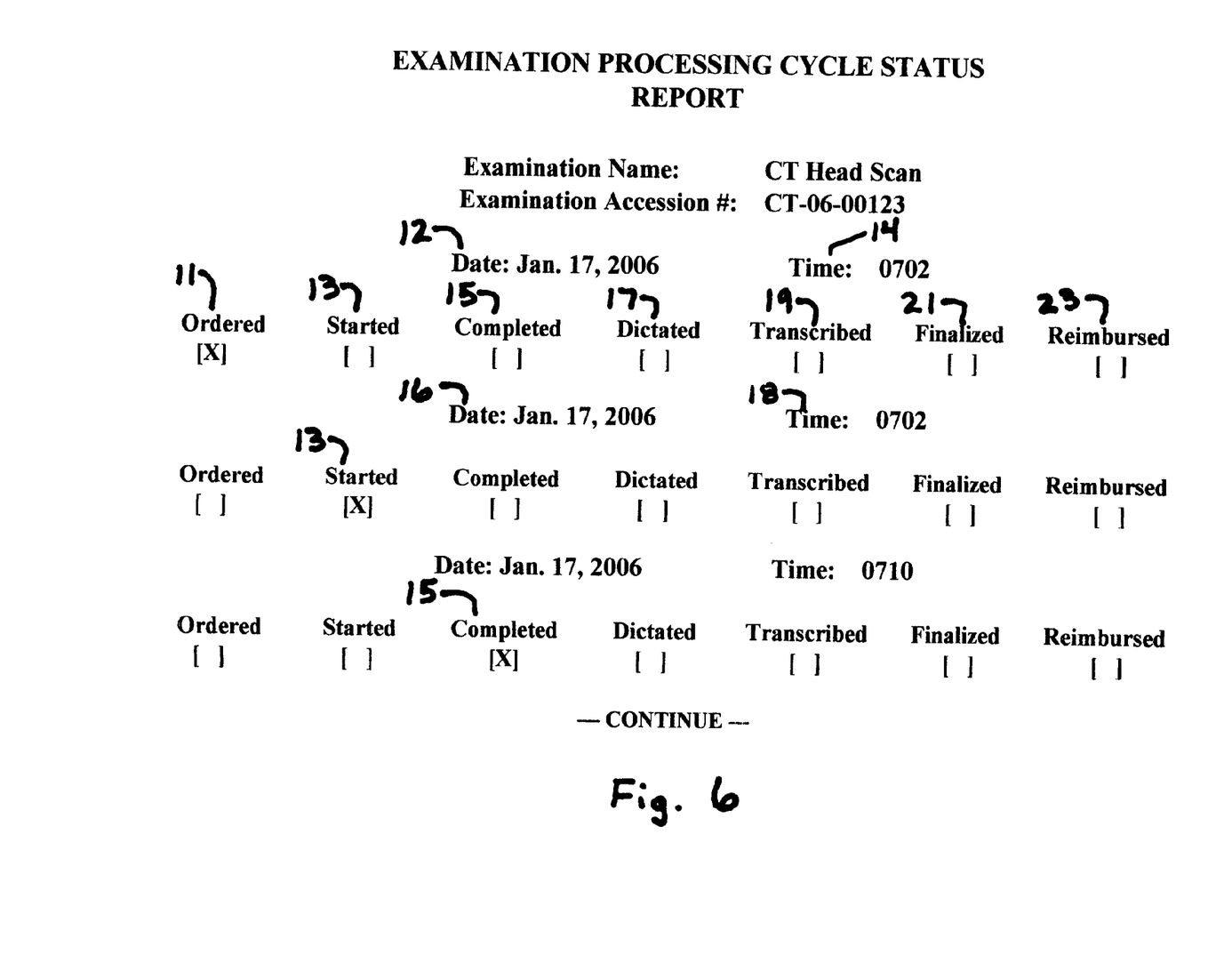
FIG. 6 is a computer screen shot of a procedure's processing cycle status report made with the apparatus of FIG. 1.

Once the technologist has performed his particular event or step correctly and the status change of procedure 22 has successfully changed from the "started" 13 status position to the "completed" 15 status position, this will indicate to the next worker in line that they can now perform his particular event or step (whatever that may be) in the processing cycle of "procedure 22" (see FIG. 6).

The next worker in line to perform an event or step in the processing cycle of "procedure 22" is the radiologist. The radiologist sees on display screen 64 that "procedure 22" is now in the "completed" 15 status position, and knows that this means that he can now perform his particular event or step of the process. The radiologist reviews the images of "procedure 22" and determines the finding. The radiologist enters data into DIS 30 via keyboard 10 that changes the status of "procedure 22" from the "completed" 15 status position to the "dictated" 17 status position. Computer 50 compares the downloaded data to a standard protocol in its memory. If the result of the comparison shows that the radiologist performed his event correctly, computer 50 may send to display screen 64 a reminder message for him to remember to do a future event, if a future event is needed. However, if the result of the comparison shows that the radiologist did not perform his event according to the standard, computer 50 may send to display screen 64 a warning message instructing him to correct this matter. There are many possibilities that may occur and for the sake of brevity I will only describe the one that follows. One example is if the radiologist after reviewing the images and recording his findings, he forgets to enter information into DIS 30 data that changes the status of "procedure 22" and indicates he has finished dictating "procedure 22" and the standard amount of time has passed that it would normally take to dictate "procedure 22", computer 50 after making a comparison may send the radiologist a message that indicates for him not to forget to change the status of "procedure 22" to the "dictated" 17 status position if he is finish with the dictation.

Once the radiologist has performed his particular event or step correctly and the status change of "procedure 22" has successfully changed there are many situations that may occur for the patient. One example has the patient being sent off to have the next scheduled ordered procedure performed. While another example could be that the radiologist entered information about his dictation that a particular area of the brain is bleeding or has a mass and due to the findings of the CT head scan or procedure 22, the radiologist has ordered another CT procedure to be performed on the patient before he leaves the department due to on area of suspicion on the pictures. The addition of the new test may cause a delay with the other scheduled ordered procedures being performed on the patient. After the newly added test is performed, the remaining scheduled test may be performed without any other interruptions.

The next worker in line to perform an event or step in the processing cycle of "procedure 22" is the transcriber. The transcriber sees on display screen 64 that "procedure 22" is now in the "dictated" 17 status position, and knows that this means that she can perform her particular event or step of the process anytime now. The transcriber enters data into DIS 30 via keyboard 10 that changes the status of "procedure 22" from the current "dictated" 17 status position to the "transcribed" 19 status position (FIG. 6). Computer 50 compares the downloaded data to a standard protocol in its memory. If the result of the comparison shows that the transcriber performed her event correctly, computer 50 may send to display screen 64 a reminder message for her to remember to do a future event, if a future event is needed. However, if the result of the comparison shows that the transcriber did not perform her event according to the standard, computer 50 may send to display screen 64 a warning message instructing her to correct this matter. It should be understood that there are many inputs or actions of the transcriber that may cause computer 50 to send the transcriber a message that indicates she has performed an event or step opposite the standard. However for the sake of brevity I will only describe the one that follows. An example of this is if the transcriber forgets to enter information into DIS 30 that changes the status of "procedure 22" and indicates to others she has transcribed the dictation of "procedure 22" and the standard amount of time has passed that it would normally take to transcribe "procedure 22", computer 50 may send the transcriber a warning message that indicates for her to enter the correct data and change "procedure 22" status position appropriately.

The next worker in line to perform an event or step in the processing cycle of "procedure 22" is the radiologist again. The radiologist sees on display screen 64 that "procedure 22" is now in the "transcribed" 19 status position, and knows that this means that he can now proof read the transcription of his dictation that was produced by the transcriber above in the processing cycle of "procedure 22". The radiologist reviews the transcribed dictation of "procedure 22" and determines if it correctly states his dictation. If the radiologist agrees with the transcribed dictation, he enters data into DIS 30 via keyboard 10 that changes the status of "procedure 22" from the "transcribed" 19 status position to the "finalized" 21 status position. Computer 50 compares the downloaded data to a standard protocol in its memory. If the result of the comparison shows that the radiologist performed his event correctly, computer 50 may send to display screen 64 a reminder message for him to remember to do a future event, if a future event is needed. However, if the result of the comparison shows that the radiologist did not perform his event according to the standard, computer 50 may send to display screen 64 a warning message instructing him to correct this matter. There are many other possibilities that may occur and for the sake of brevity I will not describe them.

The next worker in line to perform an event or step in the processing cycle of "procedure 22" is the billing person. The billing person sees on display screen 64 that "procedure 22" is now in the "finalized" 21 status, and knows that this means that she can now perform her particular event or step of the process. The billing person reviews charges for "procedure 22" and then prepares a bill accordingly. The billing person enters data into HIS 20 or DIS 30 via keyboard 10 that changes the status of "procedure 22" from the billed status position to the "reimbursed" 23 status position to complete the processing cycle. If the result of the comparison shows that the billing person performed her event correctly, computer 50 may send to display screen 64 a reminder message for her to remember to do a future event, if a future event is needed. However, if the result of the comparison shows that the billing person did not perform her event according to the standard, computer 50 may send to display screen 64 a warning message instructing her to correct this matter. There are many other possibilities that may occur and for the sake of brevity I will not describe them.

It should be understood that there are many inputs, actions or lack of actions from the workers that may cause computer 50 to send a message that instructs them to perform an event or step according to a standard.

Now, the processing cycle of "procedure 22" in the CT department is finish. A similar process of events or steps is monitored and performed by computer 50 for each department as well as each department's procedure's the patient has performed.

Figure 4:
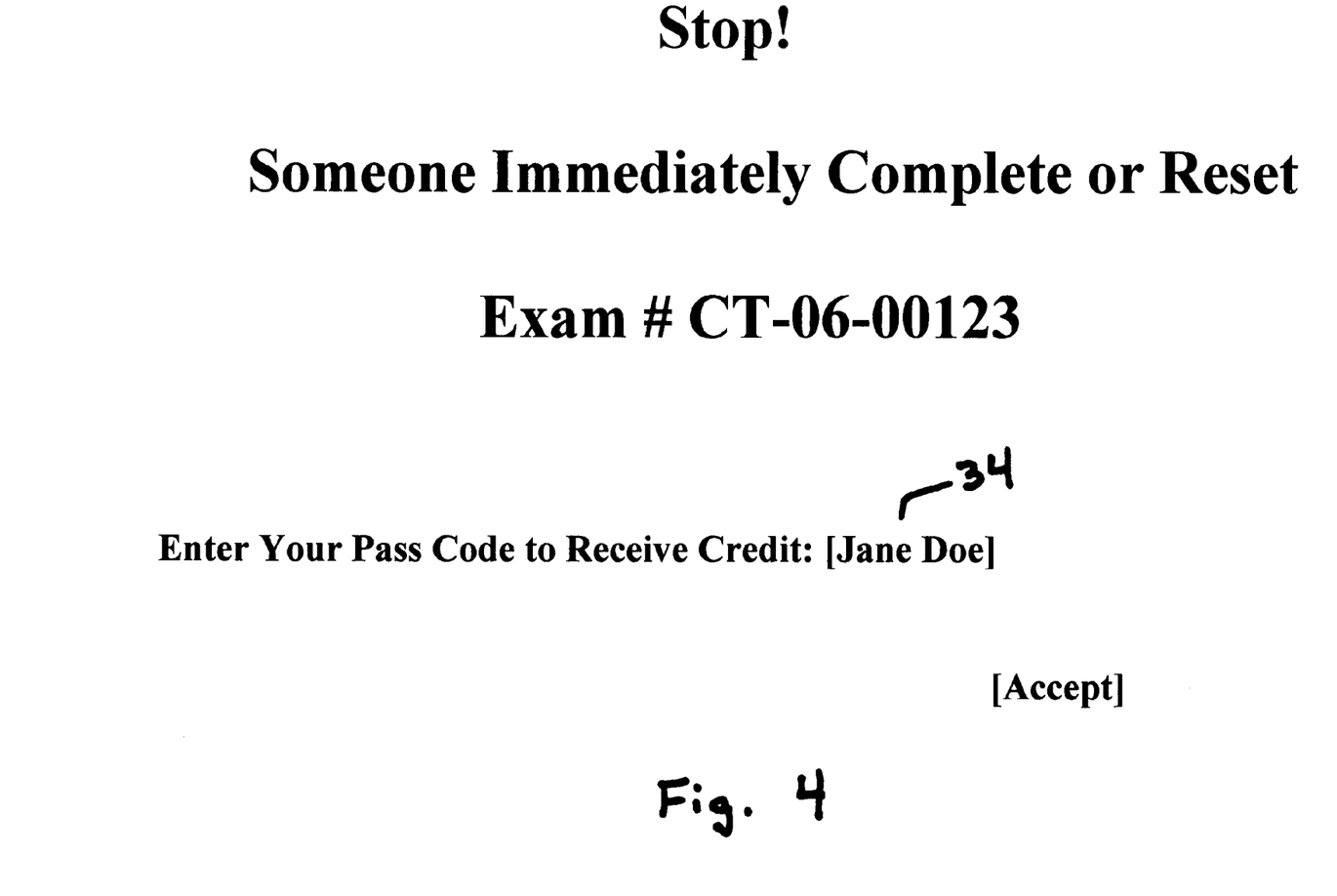
FIG. 4 is a computer screen shot of a commanding message made with the apparatus of FIG. 1.

Computer 50 or CPU 60 may be programmed to send a commanding message screen shot (see FIG. 4) that appears on display screen 64 for the worker to see and to encourage the worker to follow the message of FIG. 4 and entering their password codes to signal to management that the worker is going to fix the problem.

Computer 50 or CPU 60 may be programmed to automatically send reminder or warning messages if a worker has not entered data or some other notice that indicates he did perform his job by a certain time period.

I have described how the invention works in a CT department monitoring the processing cycle of "procedure 22" and responding to various inputs or the absence of inputs. That is the working of one department and only one of its procedures in detail. Every department has its own procedures and processing cycle which may change according to the department's needs.

As the patient goes from one department to another to have and having procedures performed, entrees are made and compared to the standard protocols to see if there are any errors or omissions in the processing cycle of each procedure.

Once the CT head scan or "procedure 22" is completed, the patient is instructed to go to x-ray and have the chest x-ray and hip x-ray procedures that are ordered performed. After the x-rays procedures are performed the patient will be instructed to go to the MRI or Lab to have all ordered procedures performed depending on which department is available.

Computer 50 or CPU 60 is programmed to arrive at many different results and findings from the comparison such as: (a) a reminder message needs to be sent to a particular worker (see FIG. 2), (b) a warning message needs to be sent to a particular worker or professional group (see FIG. 3), (c) a commanding message needs to be sent to a particular worker or professional group (see FIG. 4), etc.

Computer 50 or CPU 60 may be programmed to alarm a manager when an event is performed different than a standard protocol.

Computer 50 or CPU 60 may be programmed to alarm a manager when a particular reminder or warning message is sent to a worker or professional group.

Computer 50 or CPU 60 may be programmed to alarm a manager when a particular reminder or warning message is sent to a worker or professional group and the correct change was or was not made within a certain period of time after the prior event or step was performed.

Computer 50 or CPU 60 may be programmed to alarm a manager when an undesired amount of reminder or warning messages are being sent to a particular worker, professional group and/or about a particular event or step in the processing cycle of an examination.

Computer 50 or CPU 60 may be programmed to send a worker, professional group or manager acknowledgment once it receives data that indicates they have performed a particular event that a prior message was sent about.

The complete history of the passages of a patient through the hospital or medical facility have been received in computer 50 and compared to the protocol, various messages have been sent to enhance the efficiency, speed of treatment of the patient, any departures from the standard procedure clearly appears on the computer display or print out.

Similar test and procedures would be applied whether the patient was an outpatient who came to the hospital or an inpatient who is in a bed, in a room at the hospital.

(3) A Typical Printout for a Patient

Figure 5:
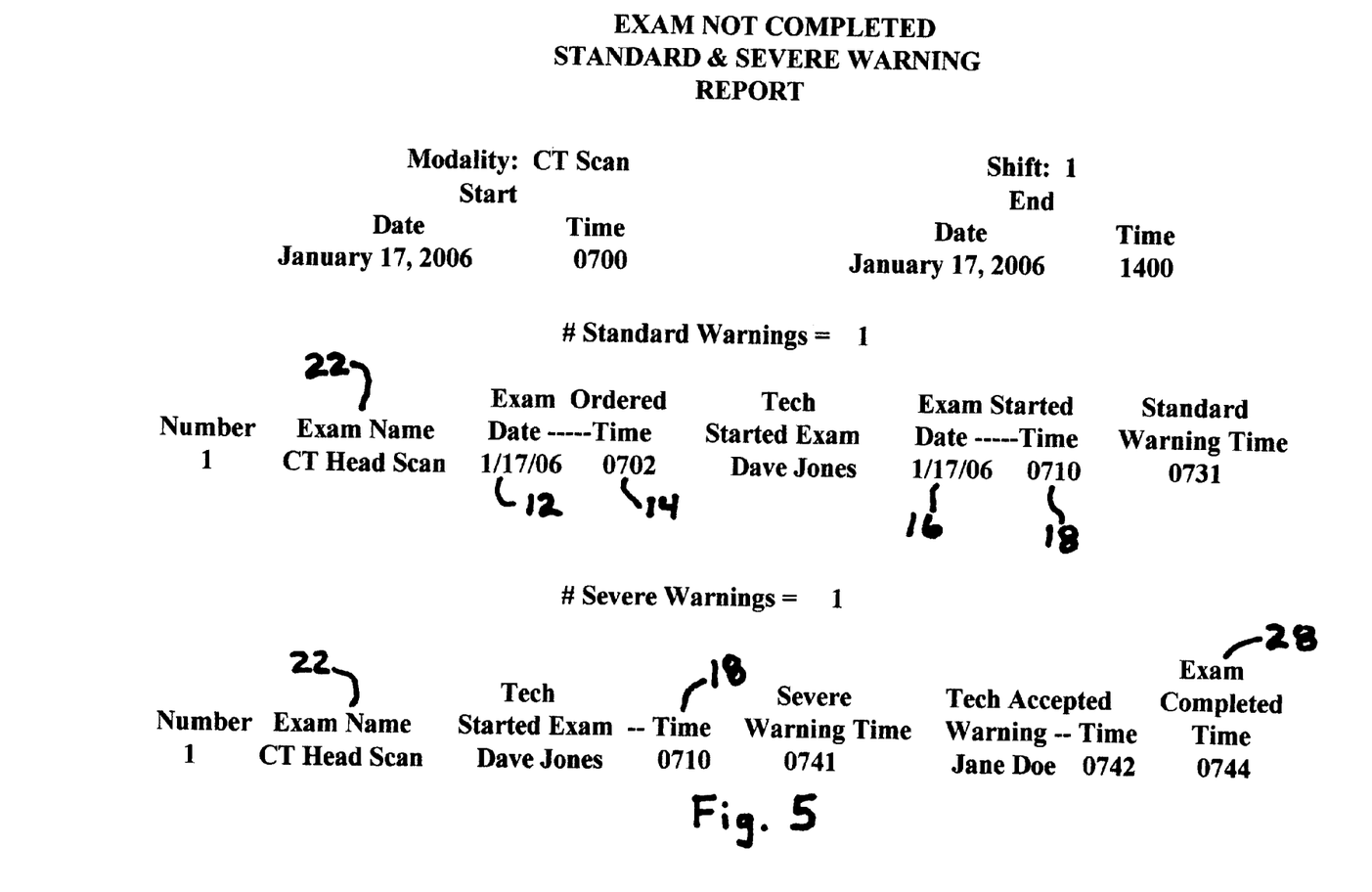
FIG. 5 is a computer screen shot of an individual event's warning report made with the apparatus of FIG. 1.

In FIG. 5 we have a printout of a typical warning message report which shows a manager which worker performed work on the patient, the nature of the work, any departures of the work from standard procedure including the time the work was and the time the message was sent.

In FIG. 6, we have a printout of the processing cycle of a typical CT examination.

Figure 7:
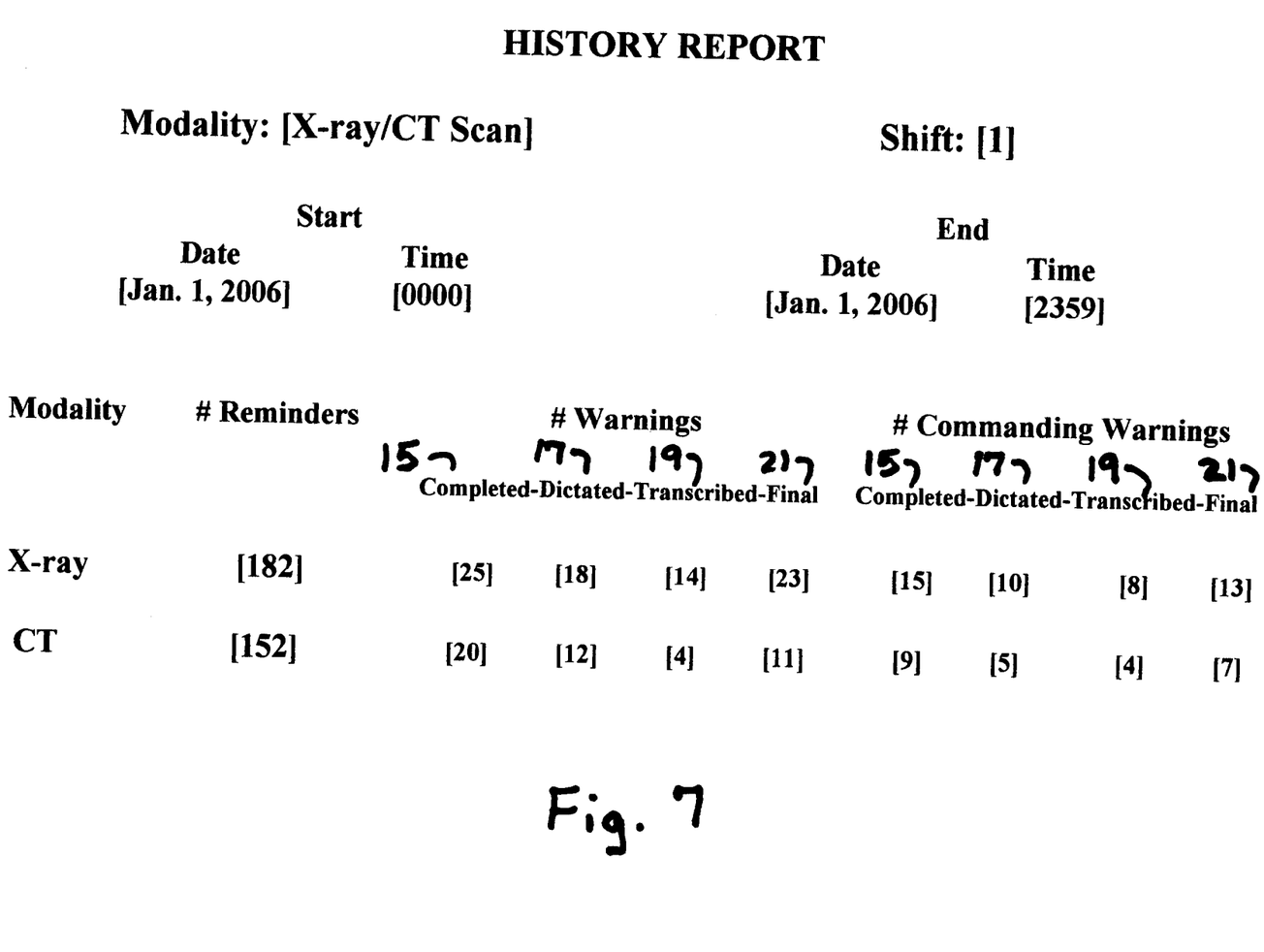
FIG. 7 is a computer screen shot of the invention's history report of reminders, warnings and commanding messages made with the apparatus of FIG. 1.

In FIG. 7, we have a printout of a typical report that shows the total number and type of messages the system sent to the X-ray Department and CT Department for a particular time period.

Computer 50 may produces a print out of procedure 22 in the form of a report that shows a manager if problems occurred during the process cycle. The print out report shows managers if money were lost performing procedure 22, on the patient.

Computer 50 is capable of producing a printout of all of the things (events) that took place about the patient from the various comparisons such as: (a) a single event or step during the processing cycle of a particular procedure or test in a single department, (b) more than one event or step during the processing cycle of a particular procedure or test in a single department, (c) one or more events or steps during the entire processing cycle of the procedures and tests a particular patient has in more than one department, etc.

A bill to the patient or the patient's insurance company may then be prepared either by computer 50 or by some person who prepares and bills from the data created by the above computer print out.

In summary each final print out will contain full data as to when each event or step of the processing cycle happened as well as how it happened.

I claim to have invented:

1. Apparatus for performing at least one of a plurality of medical procedures on a patient, each procedure being associated with at least one of a plurality of departments at a medical facility, the apparatus comprising:
    a) a computer system including a display screen, and memory which stores a plurality of procedures for at least one department at the facility, and entries from medical facility workers that order and perform events and steps involved in the processing of the procedures, wherein each procedure comprises a standard protocol involved in processing the procedure, including various events, steps, worker performance instructions, and specified amounts of time allowed for workers to perform at least one of the events and steps involved in processing the procedure;
    wherein a specified amount of time is allotted for a complete processing of a procedure, such that when any worker involved in a particular event or step of the procedure does not perform the event or step within the specified amount of time, the computer compares the actual performance time to the specified amount of time of the selected procedure and issues a warning accordingly,
    b) medical equipment for performing medical functions involved in at least one of the procedures, wherein the equipment is operated by workers in at least two different ways;
    c) said computer system having stored instructions for operating said equipment in said at least two different ways, respectively; and
    d) said computer system recording at least one of the events, steps, or functions that the workers perform during the procedure, such that at least one of the events or steps involved in the performed functions is compared with at least one of said stored instructions, thereby causing the computer system to issue a message,
    wherein, when the comparison shows that the at least one event or step was performed correctly, a reminder message including a reminder pertaining to at least one future event or step is issued, when at least one future event or step is required; and
    when the comparison shows that the at least one event or step was performed incorrectly, a warning message including instructions on how to correct the performed function is issued; and
    when a set number of warning messages are sent to a particular worker pertaining to a specific event or step performed by the worker, an alarm is issued to a manager of that particular worker indicating that the set number of warning messages have been reached.

2. The apparatus for performing at least one of a plurality of medical procedures on a patient, each procedure being associated with at least one of a plurality of departments at a medical facility as defined in claim 1, wherein said computer renders a report that shows whether or not a worker has been given a warning message.

3. The apparatus for performing at least one of a plurality of medical procedures on a patient, each procedure being associated with at least one of a plurality of departments at a medical facility as defined in claim 1, wherein, when said worker does not respond to said warning message, said computer gives notice to respond to said warning message.

4. The apparatus for performing at least one of a plurality of medical procedures on a patient, each procedure being associated with at least one of a plurality of departments at a medical facility as defined in claim 1, wherein said computer creates a report showing a worker's responses to the computer instructions.

5. A method for performing at least one of a plurality of medical procedures on a patient, each procedure being associated with at least one of a plurality of departments at a medical facility, comprising:
    a) providing a computer system including a display screen including a memory which stores more than one procedure for at least one department at the facility, and entries from medical facility workers that order or perform the procedures, wherein each procedure comprises a standard protocol involved in processing the procedure, including various events, steps, worker performance instructions, and specified amounts of time allowed for workers to perform at least one of the events and steps involved in processing the procedure;
    wherein a specified amount of time is allotted for a complete processing of a procedure, such that when any worker involved in a particular event or step of the procedure does not perform the event or step within the specified amount of time, the computer compares the actual performance time to the specified amount of time of the selected procedure in accordance with the standard protocol, and issues a warning accordingly b) providing medical equipment for performing medical functions involved in at least some of the procedures, wherein said equipment is operated by workers in at least two different way;

c) storing instructions for operating said equipment in said at least two different ways, respectively; and d) storing in said computer, some of the events and steps that the workers perform during the processing of a procedure, such that at least one of the events or steps involved is compared with at least one of said stored instructions, thereby causing a message to be issued, wherein, when the comparison shows that an event or step was performed according to said standard protocol, a reminder message including a reminder pertaining to a future event or step of the procedure is issued, when a future event or step of the procedure is required; and when the comparison shows that an event or step was not performed according to said standard protocol, a warning message indicating that the event or step was not performed according to said standard protocol is issued; and when a set number of warning messages are sent to a particular worker pertaining to a specific event or step, an alarm is issued to another worker indicating that the set number or warning messages have been reached.

6. The method for performing at least one of a plurality of medical procedures on a patient, each procedure being associated with at least one of a plurality of departments at a medical facility as defined in claim 5, wherein the computer system renders a report that shows whether or not a worker has been given a warning message.

7. The method for performing at least one of a plurality of medical procedures on a patient, each procedure being associated with at least one of a plurality of departments at a medical facility as defined in claim 5, wherein when a worker does not respond to a notification of a warning message, said computer gives notice to respond to said warning message.

8. The method for performing at least one of a plurality of medical procedures on a patient, each procedure being associated with at least one of a plurality of departments at a medical facility as defined in claim 5, wherein the computer system creates a report showing a worker's responses to said instructions.

9. An apparatus for performing events and steps involved in the processing of one or more medical procedures on a patient, each procedure being associated with at least one department at a medical facility, the apparatus comprising:

a) a computer system including a display screen, and memory which stores one or more procedures for one or more departments at the facility, and entries from medical facility workers that order and perform the processing of events and steps of the procedures, wherein each procedure comprises a standard protocol including various events, steps and worker performance instructions involved in processing the procedure;

wherein processing of a procedure is performed within a specified amount of time and there is also a specified amount of time for some events and steps to be performed within, the computer compares the actual time that a worker at the facility takes to perform an event or step, to a specified amount of time allotted in accordance with a standard protocol of the selected procedure, and when a worker does not perform the event or step within the specified amount of time, the computer issues a warning, b) medical equipment for performing medical functions involved in at least some of the procedures, wherein the equipment is operated by workers in at least two different ways;

c) said computer system having stored instructions for operating said equipment in said at least two different ways, respectively; and d) said computer system recording at least one of the events and steps that the workers perform during the processing of the procedure, such that at least one of the events or steps performed is compared with at least one of said stored instructions, thereby causing the computer system to issue a message, wherein, when the comparison shows that the event or step was performed correctly, a reminder message including a reminder pertaining to a future event or step of the procedure is issued, when a future event or step of the procedure is required; and when the comparison shows that the event or step was performed incorrectly, a warning message including instructions on how to correct the event or step is issued; and when a set number of warning messages are sent to a particular worker pertaining to a specific event or step in the process, an alarm is issued to a manager of that particular worker indicating that the set number of warning messages has been reached.

10. The apparatus for performing the events and steps involving the processing of one or more medical procedures on a patient, each procedure being associated with at least one department at a medical facility as defined in claim 9, wherein said computer renders a report that shows when a worker has been given a warning message.

11. The apparatus for performing the events and steps involving the processing of one or more medical procedures on a patient, each procedure being associated with at least one department at a medical facility as defined in claim 9, wherein when a worker does not respond to the notification of a warning message, said computer alerts another worker to respond to the notification.

12. The apparatus for performing the events and steps involving the processing of one or more medical procedures on a patient, each procedure being associated with at least one department at a medical facility as defined in claim 9, wherein said computer creates a report showing a worker's responses to the computer instructions.

* * * * *